(12) United States Patent
Nam et al.

(10) Patent No.: US 10,974,099 B2
(45) Date of Patent: Apr. 13, 2021

(54) EXERCISE EQUIPMENT APPARATUS AND METHOD FOR PREVENTING MANIPULATION OF EXERCISE DATA

(71) Applicant: Hyun Jin Kim, Seongnam-si (KR)

(72) Inventors: Kang Won Nam, Seongnam-si (KR); Sung Chul Leem, Siheung-si (KR)

( * ) Notice: Subject to any disclaimer, the term of this patent is extended or adjusted under 35 U.S.C. 154(b) by 669 days.

(21) Appl. No.: 15/736,773

(22) PCT Filed: Jun. 13, 2016

(86) PCT No.: PCT/KR2016/006249
§ 371 (c)(1),
(2) Date: Dec. 14, 2017

(87) PCT Pub. No.: WO2016/208898
PCT Pub. Date: Dec. 29, 2016

(65) Prior Publication Data
US 2018/0169475 A1    Jun. 21, 2018

(30) Foreign Application Priority Data
Jun. 25, 2015  (KR) .......................... 10-2015-0090255

(51) Int. Cl.
*A63B 24/00* (2006.01)
*A63B 22/02* (2006.01)

(52) U.S. Cl.
CPC .......... *A63B 24/0087* (2013.01); *A63B 22/02* (2013.01); *A63B 24/0006* (2013.01);
(Continued)

(58) Field of Classification Search
CPC . A63B 24/0087; A63B 22/02; A63B 24/0006; A63B 24/0062
(Continued)

(56) References Cited

U.S. PATENT DOCUMENTS

| 6,539,336 B1 * | 3/2003 | Vock .................... A42B 3/0433 702/178 |
| 2007/0057779 A1 * | 3/2007 | Battista .................... G08G 1/20 340/425.5 |

(Continued)

FOREIGN PATENT DOCUMENTS

| CN | 103418126 | 12/2013 |
| CN | 103100202 | 5/2015 |

(Continued)

OTHER PUBLICATIONS

Cochrane, "Vibration Exercise:The Potential Benefits", Oct. 2010, Massey University, pp. 75-99 (Year: 2010).*

(Continued)

*Primary Examiner* — Taghi T Arani
*Assistant Examiner* — Gregory A Lane
(74) *Attorney, Agent, or Firm* — Antonio Ha U.S. Patent, LLC

(57) ABSTRACT

Some embodiments of the present specification relate to an apparatus for preventing the manipulation of exercise data, the apparatus comprising: a sensor installed in a driving unit of an exercise equipment or at a position close to the driving unit, to sense vibration associated with the exercise of a user; a storage unit for recording and storing a reference value for determining whether exercise data has been manipulated, according to an operational feature of the exercise equipment; an exercise data determining unit for determining whether the exercise data of the user has been manipulated, by comparing a vibration measurement value of the exercise equipment measured by the sensor with the reference value when driving of the exercise equipment is identified; and a control unit for performing control to receive exercise equipment information from which the user may determine a unique feature of the exercise equipment to which the user logs on, extract the reference value corresponding to the
(Continued)

exercise equipment from the storage unit, receive a result of determining whether the exercise data of the user is normal, from the exercise data determining unit, store the received exercise data when it is determined that the exercise data is normal, and not store the exercise data when it is determined that the exercise data is abnormal.

12 Claims, 10 Drawing Sheets

(52) U.S. Cl.
CPC ...... *A63B 24/0062* (2013.01); *A63B 2220/30* (2013.01); *A63B 2220/51* (2013.01); *A63B 2220/64* (2013.01); *A63B 2225/50* (2013.01)

(58) Field of Classification Search
USPC .......................................................... 726/26
See application file for complete search history.

(56) References Cited

U.S. PATENT DOCUMENTS

| | | | | |
|---|---|---|---|---|
| 2007/0219059 | A1* | 9/2007 | Schwartz | G06F 19/3481 482/8 |
| 2008/0207401 | A1* | 8/2008 | Harding | A63B 24/0006 482/4 |
| 2008/0234107 | A1 | 9/2008 | Cox et al. | |
| 2009/0048070 | A1* | 2/2009 | Vincent | A63F 13/02 482/8 |
| 2009/0111656 | A1 | 4/2009 | Sullivan et al. | |
| 2012/0142496 | A1* | 6/2012 | Tsarpela | A63B 21/4033 482/1 |
| 2013/0274066 | A1 | 10/2013 | Ashby et al. | |
| 2014/0038777 | A1* | 2/2014 | Bird | A63B 21/151 482/5 |
| 2014/0113261 | A1* | 4/2014 | Akiba | A63B 23/0405 434/247 |

FOREIGN PATENT DOCUMENTS

| | | |
|---|---|---|
| KR | 10-0819205 | 4/2008 |
| KR | 10-2015-0008534 | 4/2015 |

OTHER PUBLICATIONS

English specification of 10-0819205.
English specification of 10-2015-0008534.
English Specification of 103418126.
English Specification of 103100202.

* cited by examiner

EXERCISE EQUIPMENT APPARATUS AND METHOD FOR PREVENTING MANIPULATION OF EXERCISE DATA

CROSS-REFERENCE TO RELATED APPLICATIONS

This patent application is a national-stage application of International Patent Application No. PCT/KR2016/006249, filed on Jun. 13, 2016 which claims priority under 35 U.S.C. § 119 to Korean Patent Application No. 10-2015-0090255, filed on Jun. 25, 2015, in the Korean Intellectual Property Office, the disclosure of which is incorporated by reference herein in its entirety.

TECHNICAL FIELD

This disclosure relates to exercise equipment capable of measuring the user's amount of exercise, and specifically to, exercise equipment and methods capable of preventing the user from intentionally manipulating his/her exercise data.

DISCUSSION OF RELATED ART

With drastic changes and growth in society, modern people have a less chance of leisure or outdoor activity and workout. Thus, obesity is commonplace and remarkable.

To address such issue, various types of fitness machines are being developed, e.g., treadmills, rowing machines, steppers, cycling machines, indoor cycling bikes, air walk trainers, or other indoor exercise equipment. Such fitness equipment may present maximum exercise effects even in a narrow space.

However, conventional indoor exercise machines merely allow users to repeat simple operations, which is quite boring, deterring them from keeping exercising. Thus, brand-new types of fitness machines are coming to the market, such as ones that may provide and vary videos and sounds depending on speeds, most of which, however, simply keep displaying the same video or still bore the user.

An alternative is exergame exercise equipment that enable the user to enjoy while playing console or video game, e.g., playing screen golf.

Meanwhile, the growth of healthcare industry leads to the need for creating personal exercise data into a database for future use as diagnostic information or medical information for preventing various chronic diseases, e.g., extreme obesity.

Such services are recently spreading as indoor fitness machine manufacturers accrue users' exercise data in their database and provide the information. The garnered exercise information may be of high significance that may be demanded not only by sports centers, pharmaceutical companies, health insurance companies, or other healthcare companies, but also by governmental organization. A service predictable to come in near future is discounting insurance using private exercise data. The following scenario may be possible, for example: an insurer provides an exercise mission to someone, periodically gathers his exercise data, determine whether he has completed the mission, and reflects the same in determining insurance fees.

As such, exact measurement and utilization of exercise data may be very critical in healthcare industry. However, conventional techniques for collecting exercise data cannot prevent users' intentional manipulation. For example, wearable devices which are widely used as fitness trackers may produce exercise information that does not match the actual amount of exercise, due to intentional movements or motions. Data manipulation may also arise when the user does not work out while the fitness machine continues to work. In such case, the healthcare service may suffer from a deterioration of reliability and quality.

SUMMARY

An embodiment of the present disclosure aims to provide a fitness machine and method capable of preventing the user from intentionally manipulating exercise data.

According to a first embodiment of the present disclosure, a method for analyzing a user's exercise data generated from a fitness machine comprises the steps of receiving the user's login information, identifying fitness machine information for identifying a unique feature of the fitness machine to which the user logs in, identifying a reference value for determining whether the exercise data is manipulated as per the feature of the fitness machine through the fitness machine information, determining whether the fitness machine is driven, if the fitness machine is identified to be driven, identifying a vibration measurement obtained for the fitness machine through a vibration sensor for a predetermined time, and determining whether the user's exercise data is manipulated by comparing the identified vibration measurement with the reference value.

According to a second embodiment of the present disclosure, a method for analyzing a user's exercise data generated from a human-powered fitness machine comprises the steps of receiving the user's login information, identifying fitness machine information for identifying a unique feature of the fitness machine to which the user logs in, identifying a reference value for determining whether the exercise data is manipulated as per the feature of the fitness machine through the fitness machine information, measuring exercise speed data generated through driving of the fitness machine at each predetermined period, and comparing a deviation between pieces of the measured exercise speed data with the reference value to determine whether the user's exercise data is manipulated.

According to the first embodiment of the present disclosure, a device for analyzing a user's exercise data generated from a fitness machine comprises a sensor mounted in or near a driver of the fitness machine to detect a vibration as per the user's exercise, a storage unit storing a reference value for determining whether the exercise data is manipulated as per a driving feature of the fitness machine, an exercise data determiner comparing a vibration measurement obtained for the fitness machine through the sensor with the reference value to determine whether the user's exercise data is manipulated if the fitness machine is identified to be driven, and a controller receiving fitness machine information for identifying a unique feature of the fitness machine, extracting the reference value corresponding to the fitness machine from the storage unit, receiving a result of determining whether the user's exercise data is normal from the exercise data determiner, and performing control to store the received exercise data if the exercise data is determined to be normal and not to store the received exercise data if the exercise data is determined to be abnormal.

According to the second embodiment of the present disclosure, a device for analyzing a user's exercise data generated from a human-powered fitness machine comprises an exercise speed measuring unit measuring a driving speed of the fitness machine, a storage unit storing a reference value for determining whether the exercise data is manipulated as per a driving feature of the fitness machine, an exercise data determiner measuring, at each predetermined period, exercise speed data generated through driving of the fitness machine and comparing a deviation between pieces of the measured exercise speed data with the reference value to determine whether the user's exercise data is manipulated, and a controller receiving fitness machine information for identifying a unique feature of the fitness machine, extracting the reference value corresponding to the fitness machine from the storage unit, receiving a result of determining whether the user's exercise data is normal from the exercise data determiner, and performing control to store the received exercise data if the exercise data is determined to be normal and not to store the received exercise data if the exercise data is determined to be abnormal.

According to some embodiments of the present disclosure, there are provided fitness machines and methods for preventing users from intentionally manipulating exercise data.

By preventing users' intentional exercise data manipulation, the healthcare services may have higher reliability, enabling the exercise data to be actively and widely utilized in various sectors, e.g., medical, insurance, and financial sectors.

DETAILED DESCRIPTION OF EMBODIMENTS

Figure 1:
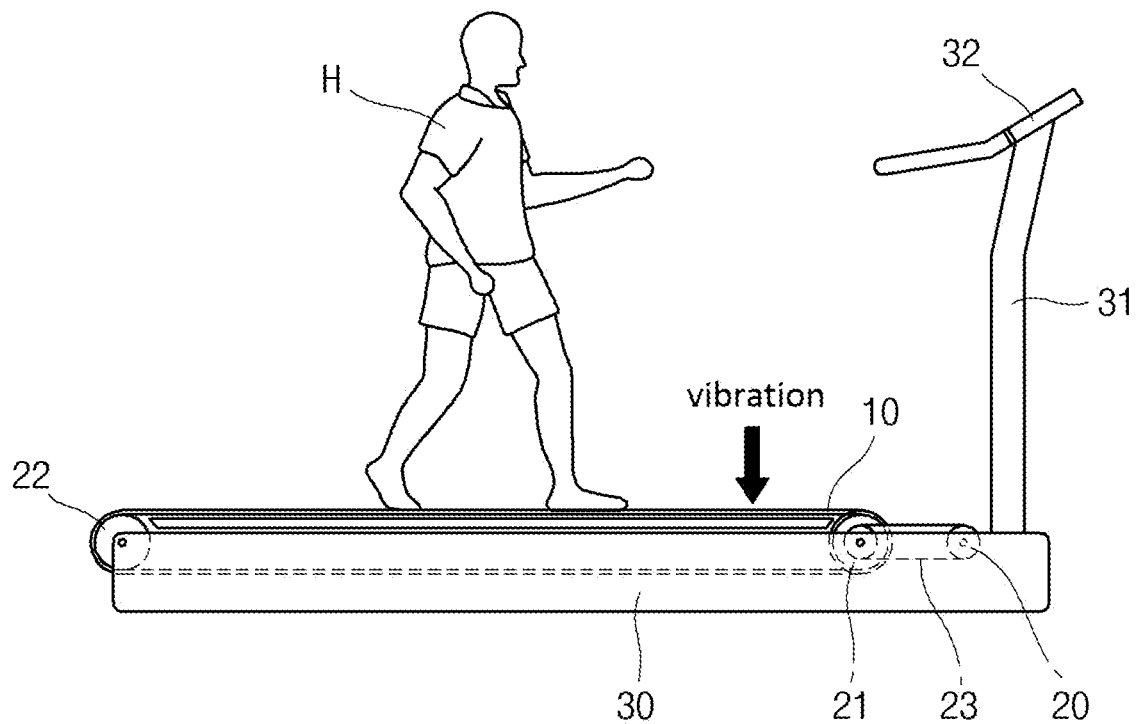
FIG. 1 is a view schematically illustrating a fitness machine according to an embodiment of the present disclosure.

Hereinafter, embodiments of the present disclosure are described in detail with reference to the accompanying drawings.

Techniques irrelevant with the disclosure or well known in the art to which the present disclosure pertains are skipped from the description of the embodiments to convey the subject matter of the present disclosure in a further clarified manner.

For the same reasons, some components in the drawings are exaggerated or omitted or schematically illustrated. The size of each component does not completely reflect its actual size. The same reference denotations are used to refer to the same or equivalent components in the drawings.

According to an embodiment of the present disclosure, the irregularity of a human being who is using a fitness machine is used to prevent manipulation of exercise data in the fitness machine. Generally, a machine is used to manipulate exercise data from the fitness machine. At this time, given the driving characteristics of the fitness machine, whether the exercise data is manipulated may be determined in two types. For example, an exercise device, which has a power machine, e.g., a motor, and a stepper or cycling machine, which is driven by a human being's power, have different driving characteristics. Whether exercise data is manipulated may be determined considering such driving characteristics. For example, in the case of treadmills, one may log into an exercise data service for measuring the amount of exercise with his personal ID to operate the treadmill. In this case, he may easily manipulate exercise data even without doing exercise. Where the treadmill has a sensor capable of one's exercise, it is possible to copy vibrations generated by one's exercise using the motor. However, irregular periods are observed when one actually does exercise. Accordingly, the irregularity of exercise data may serve as a reference for distinguishing between human being and machine. Further, fitness machines, such as cycling machines or elliptical trainers, are operated by human power. Thus, such fitness machines are required to be operated by an external power machine, e.g.; a motor, to manipulate exercise data in the fitness machines. In other words, if the fitness machine is operated by a separate power machine to manipulate exercise data, the speed of exercise measured for the fitness machine is rendered very constant. In contrast, when a human being actually does exercise, the speed of exercise entails more or less fluctuations. Thus, preventing manipulation of exercise data in the human-powered fitness machines requires a series of steps of obtaining speeds at predetermined cycles and determining that data has been manipulated when deviations in speed is too constant.

FIG. 1 is a view schematically illustrating a fitness machine according to an embodiment of the present disclosure, wherein as a representative example of the fitness machine, a treadmill is shown.

As shown, the treadmill includes a running belt 10, a driving motor 20, and a body unit 30.

A frame 31 is formed on a side of the body unit 30. A control panel 32 having, e.g., buttons for the user's control is formed on the frame 31.

The running belt 10 is rotated by a pair of rollers 21 and 22 installed inside the body unit 30 and may be constituted of a belt supporting the user H. One 21 of the rollers is connected with the driving motor 20 to receive rotational power from the motor. The driving motor 20 and the roller 21 are connected together via a rotational power delivery belt 23.

The user H may choose an exercise mode, e.g., walking or miming, and do exercise on the running belt 10, and the user may measure the rotational motion of the driving motor 20 or the roller 21 to measure the amount of exercise of the user H. At this time, if the user H starts exercise as the fitness machine is driven, vibrations naturally occur.

However, if the user H drives the fitness machine and keeps the running belt 10 operating without the user H aboard, no vibrations would occur. Or, if the user uses a vibrator to fake his exercise as if he actually does exercise aboard, irregular, meaningful vibration signals would not be sensed which otherwise would be. According to an embodiment of the present disclosure, such nature is taken into account to detect manipulation of exercise data.

Figure 2:
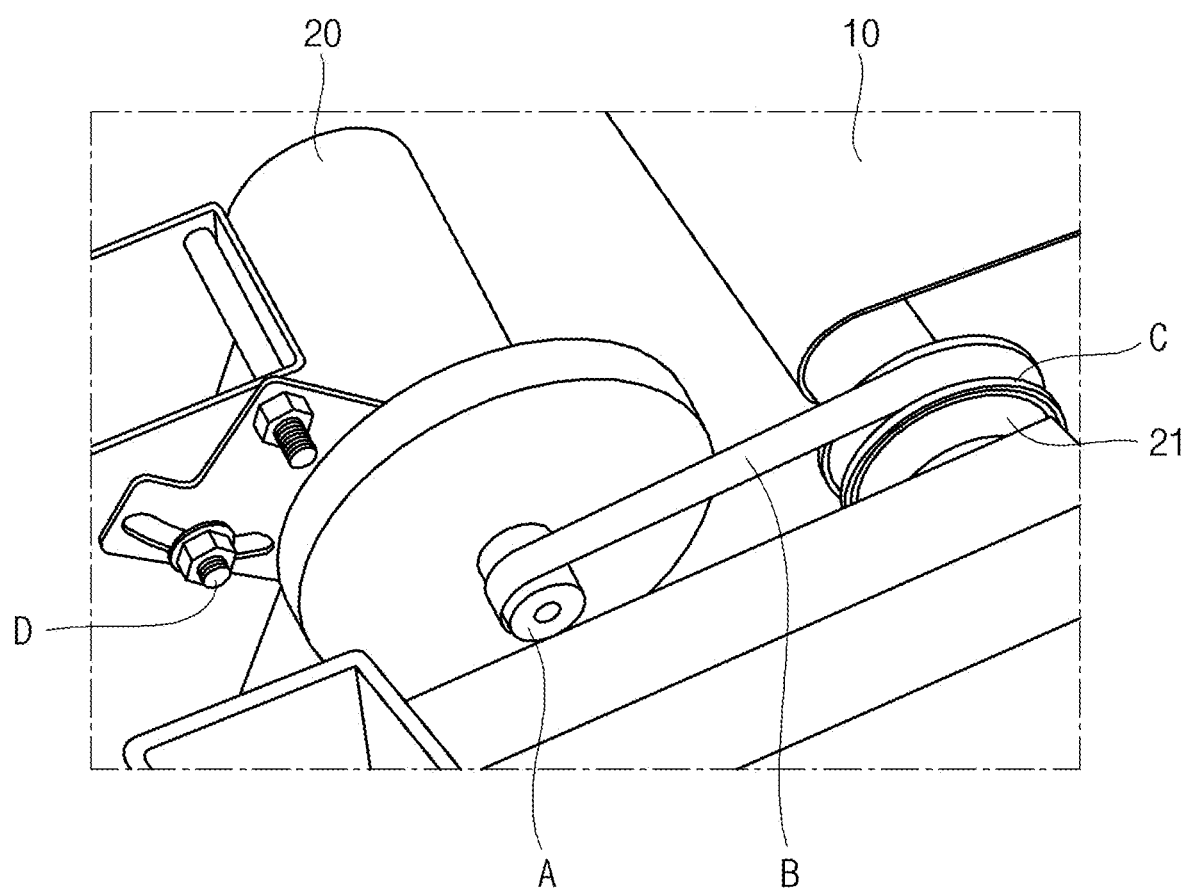
FIG. 2 is a reference view illustrating a position in which a sensor is mounted according to an embodiment of the present disclosure.

FIG. 2 is a reference view illustrating a position where a sensor is mounted according to an embodiment of the present disclosure.

As mentioned above, the treadmill is an exercise machine that uses power from the motor 20 to allow the user to passively do exercise. If it lacks a special device for detecting the user's exercise, it easily permits the user to manipulate his exercise information. As an example, after logging in with his user ID, the user may operate the treadmill. If the user gets down the treadmill, his amount of exercise would increase, i.e., amount-of-exercise information would be manipulated. If the manipulated data is stored in the server, the reliability of the healthcare service would be deteriorated. To address such issue, a vibration sensor may be provided in a predetermined position (A, B, C, or D) of the treadmill to detect vibrations generated when the user actually walks or runs, thereby enabling determination as to whether he really does exercise.

The predetermined position (A, B, C, or D) where the sensor is mounted may be the best one where vibrations generated by the user's exercise may be detected. According to an embodiment of the present disclosure, the position may be a portion of the part assembled with the mill (which is the rub band portion rotated by the roller) where vibrations are generated most by the user's exercise.

Figure 3:
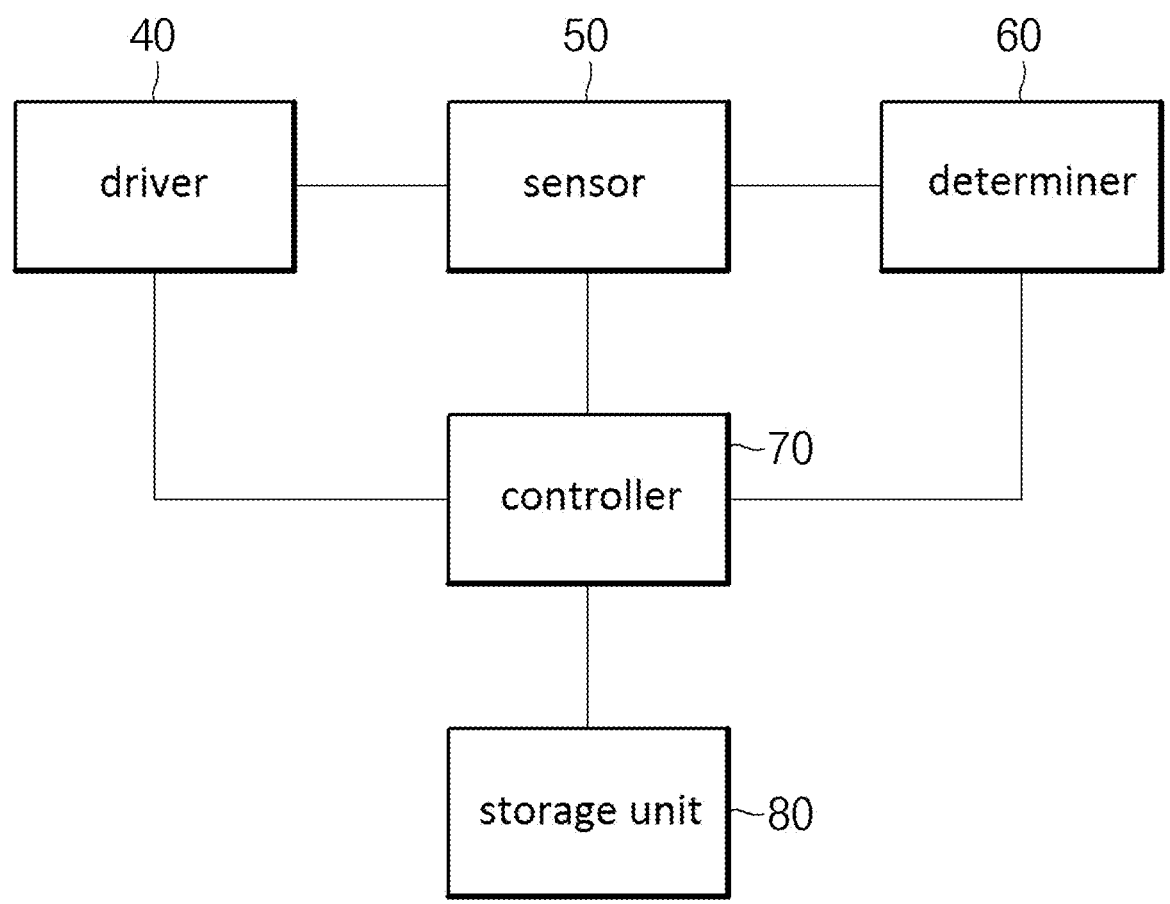
FIG. 3 is a block diagram schematically illustrating a configuration of a device for preventing manipulation of exercise data according to an embodiment of the present disclosure.

FIG. 3 is a block diagram schematically illustrating a configuration of a device for preventing manipulation of exercise data according to an embodiment of the present disclosure.

As shown, an exercise data manipulation preventing device according to an embodiment of the present disclosure includes a driver 40, a sensor 50, a determiner 60 for determining whether exercise data is manipulated, a controller 70, and a storage unit 80.

The driver 40 may be a driving motor for treadmills or similar exercise machines, or a rotor that causes loads as per one's motion or movement if the exercise machine is a human-powered one, such as a cycling machine or stepper.

The sensor 50 includes a vibration sensor, a load sensor, or a speed sensor.

The vibration sensor is provided in or near the driver 40 of the fitness machine to detect vibrations generated by the user's exercise. As described above in connection with FIG. 2, the vibration sensor may be mounted in a portion (A, B, C, or D) of the part assembled with the mill (which is the rub band portion rotated by the roller) where vibrations are most frequently generated by the user's exercise.

The load sensor or speed sensor may be installed in the rotor where loads are caused, or speed is varied by the user's motion.

The storage unit 80 records or stores reference values for determining whether exercise data is manipulated according to the driving characteristics of the fitness machine.

Here, the reference values may be a reference by which the unique properties of the fitness machine may be grasped per type, manufacturer, or model. The reference values may previously be set as per manufacturing date, manufacturer, or model name and stored in the storage unit.

Upon identifying that the fitness machine is driven, the determiner 60 compares a fitness machine measurement obtained by the sensor 50 with a reference value, determining whether the user has manipulated his exercise data.

According to an embodiment of the present disclosure, to determine whether exercise data is manipulated in the treadmill, the determiner 60, upon identifying that the treadmill is driven, identifies a vibration value of the fitness machine, which is measured by the vibration sensor of the fitness machine, for a predetermined time, and compares the identified vibration value with a reference value to determine whether the user has manipulated his exercise data. Or, the determiner 60 may determine the regularity of periods when the peaks of the vibration measurements occur, and determine that the exercise data is normal if it is irregular and that the exercise data has been manipulated if it is substantially regular.

According to an embodiment of the present disclosure, to determine whether exercise data is manipulated in a human-powered fitness machine, the determiner 60 may measure, at each predetermined period, exercise speed data generated as the fitness machine is drive and compare a deviation between pieces of exercise speed data measured with a reference value to determine whether the user has manipulated his exercise data.

A more detailed method for determining whether exercise data is manipulated is described below with reference to FIGS. 5 to 10.

The controller 70 may perform control to receive fitness machine information for identifying unique properties of the fitness machine, to extract a reference value corresponding to the fitness machine from the storage unit 80, to receive a result of determining whether the user's exercise data is normal from the determiner 60, and to store the received exercise data if the exercise data is determined to be normal and not to store the received exercise data if the exercise data is determined to be abnormal.

The exercise data manipulation preventing device may be integrally formed with the fitness machine or may be configured in the fitness machine in the form of a module.

Figure 4:
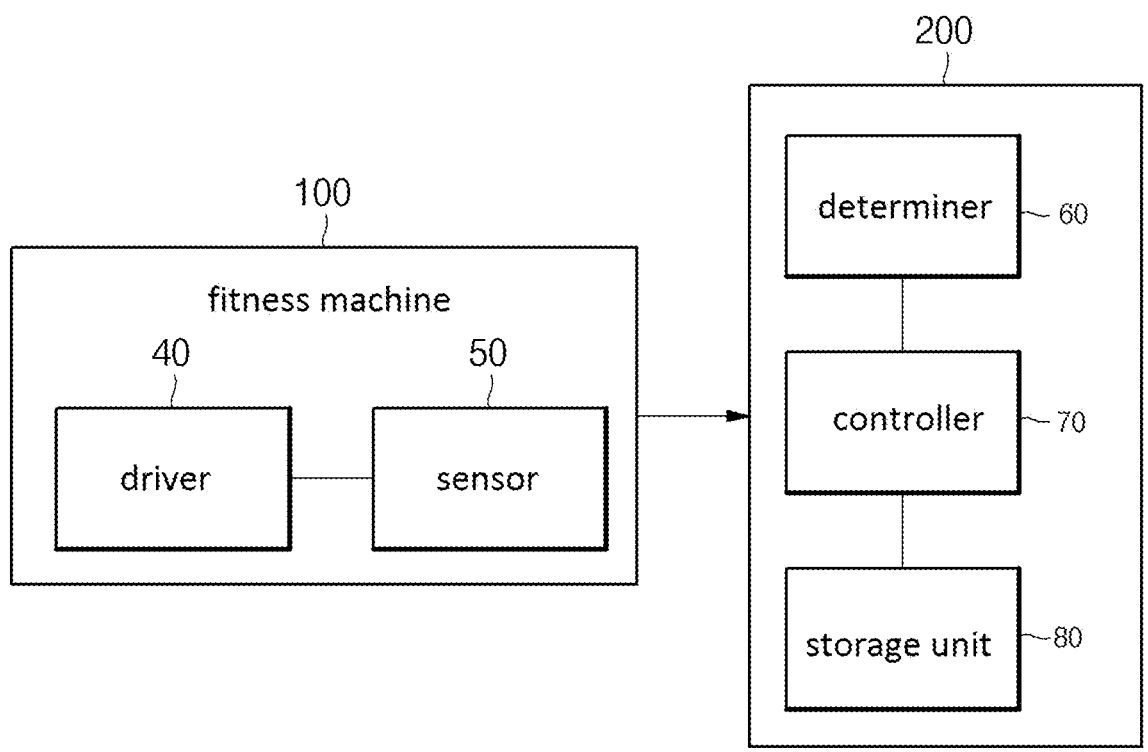
FIG. 4 is a block diagram schematically illustrating a configuration of a device for preventing manipulation of exercise data according to another embodiment of the present disclosure.

FIG. 4 is a block diagram schematically illustrating a configuration of a device for preventing manipulation of exercise data according to another embodiment of the present disclosure.

As shown, the exercise data manipulation preventing device 200 may be configured separate from the fitness machine 100.

That is, the electronic device manipulation preventing device 200 may be wiredly or wirelessly connected with the fitness machine 100 including a driver 40 and a sensor 50 to receive sensor data for identifying exercise data generated from the fitness machine 100 and the truth of the data.

In this embodiment, the exercise data manipulation preventing device 200 may be configured in the form of a cloud server which is connected via a network with multiple fitness machines, thus serving as a managing server that identifies the truth of exercise data and manages the user's exercise data in database.

Figure 5:
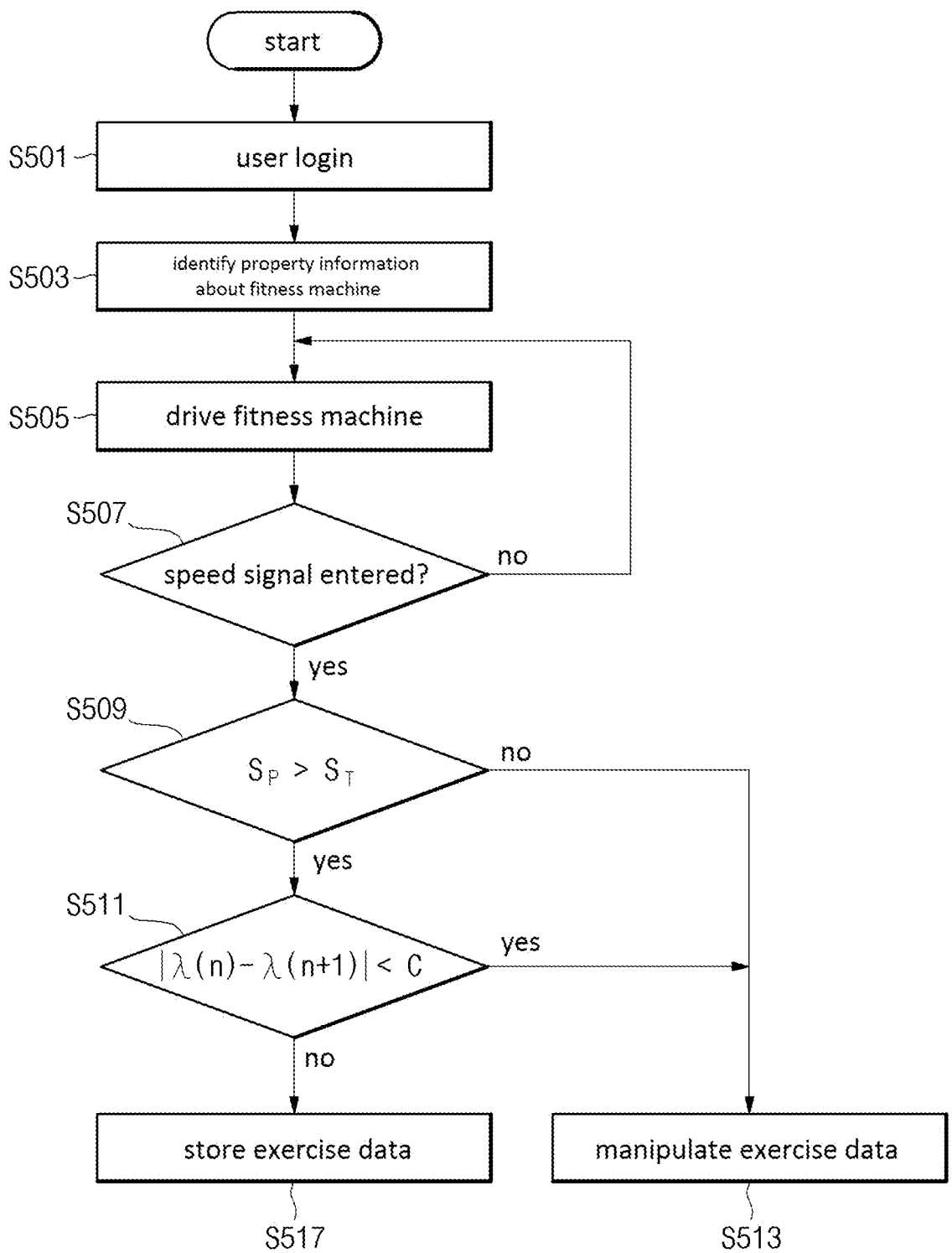
FIG. 5 is a block diagram schematically illustrating sequentially a method for preventing manipulation of exercise data according to a first embodiment of the present disclosure.

FIG. 5 is a flowchart sequentially illustrating a method for preventing manipulation of exercise data according to a first embodiment of the present disclosure, wherein an example of applying the method to a treadmill is shown as an example.

First, the exercise data manipulation preventing device receives login information from the user (S501). The user may continuously enter his exercise data to the database and manage the exercise data by logging into his account and doing exercise. Or, if he uses an exer-gaming fitness machine, he may log in and enjoy game and exercise or hold a competition or event with other users.

The exercise data manipulation preventing device identifies fitness machine information for identifying unique features of the fitness machine for which the user logs in (S503). The fitness machine information may include the model number, ID, or serial number of the fitness machine or any other unique information from which the features of the fitness machine may be identified.

The storage unit 80 of the exercise data manipulation preventing device records or stores reference values for determining whether exercise data is manipulated as per the driving characteristics of the fitness machine. Here, the reference values may be a reference for grasping the unique features of the fitness machine per type, manufacturer, or model of the fitness machine, and the reference values may previously be stored per date of manufacture, manufacturer, or model and stored in the storage unit. Accordingly, the unique features of the fitness machine may be grasped through the fitness machine information, and reference values corresponding to the grasped unique features may be extracted.

Thereafter, if the fitness machine is driven, exercise data is entered (S505).

It is determined whether the entered exercise data includes a speed signal (S507). If no speed signal is entered, the fitness machine is determined to be not driven, and if a speed signal is entered, the driving of the fitness machine is identified, and measurements for vibrations generated from the fitness machine which are obtained by the vibration sensor of the fitness machine are identified for a predetermined time.

The identified vibration measurement SP is compared with a reference value (i.e., a vibration threshold ST) which indicates the minimum vibration from which the user may be determined to be doing exercise (S509).

As a result of the comparison in step S509, if a speed signal is entered from the fitness machine but no vibration measurement is entered or if a value smaller than the vibration threshold ST indicating the minimum vibration from which the user may be determined to be doing exercise is entered, the exercise data is determined to have been manipulated or to be abnormal (S513).

Figure 6:
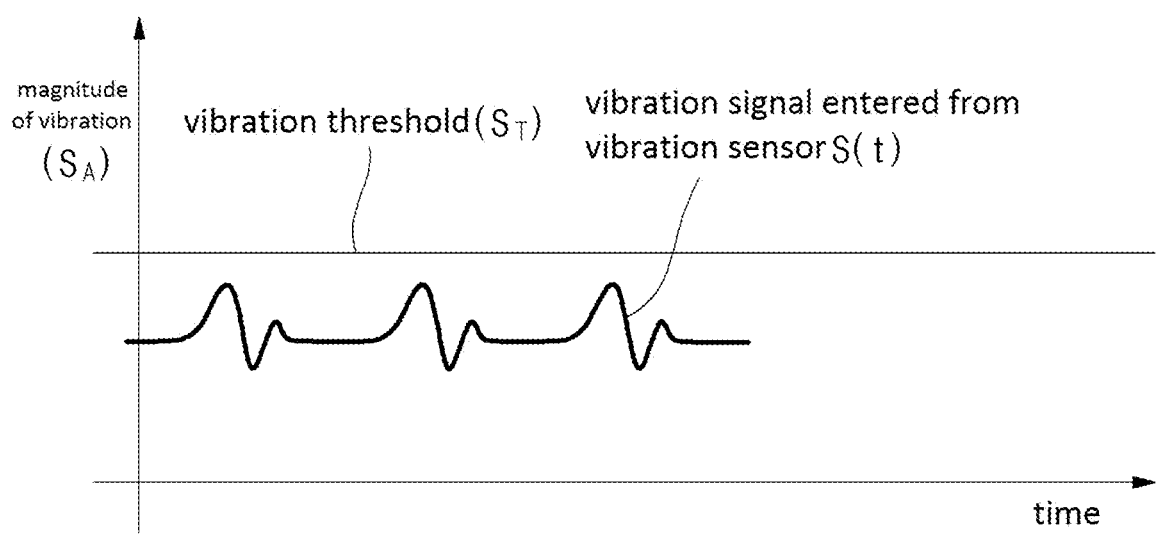
FIG. 6 is a reference view illustrating an example where exercise data has been manipulated in the embodiment of FIG. 5.

FIG. 6 is a view illustrating a vibration signal (S(t)) observed when a speed signal is entered but the vibration signal is smaller than a threshold.

Here, the vibration threshold ST is a value that may vary depending on the properties of the fitness machine. The vibration threshold may previously be set and stored in the storage unit, and the optimal one of vibration thresholds set depending on contexts may be chosen and used.

Where a vibration signal as shown in FIG. 6 is entered, the vibration may be determined to have originated from ambient noise, but not from the user's exercise, which may be considered as being not in the situation where the user actually uses the fitness machine and enters exercise data.

As a result of the comparison in step S509, where a value larger than the vibration threshold ST indicating the minimum vibration from which the user may be determined to be doing exercise is entered, the exercise data may be determined to be normal and the entered exercise data may be stored.

Figure 7:
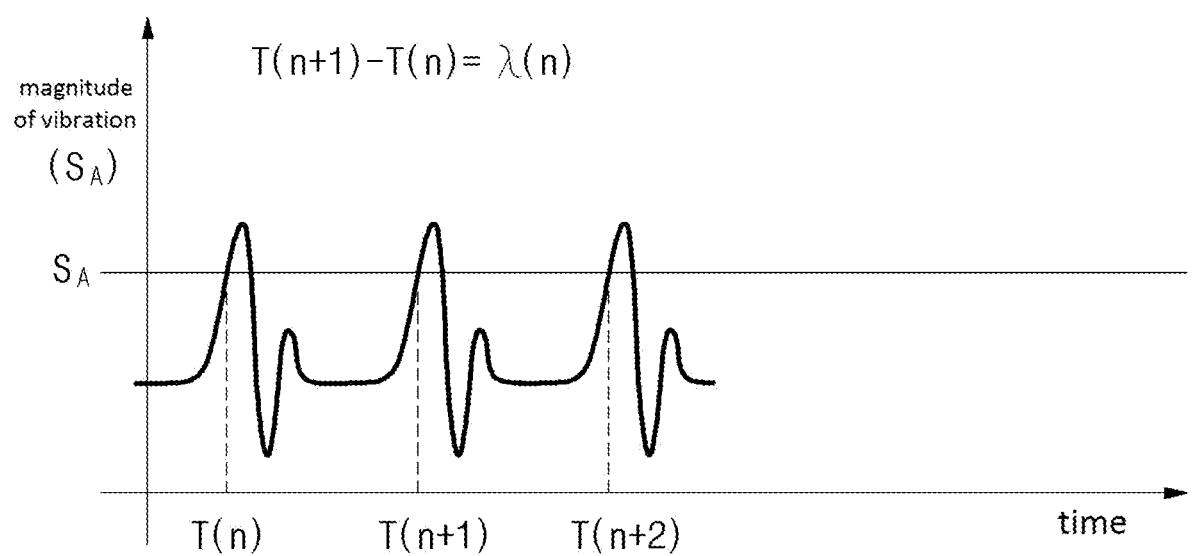
FIG. 7 is a reference view illustrating another example where exercise data has been manipulated in the embodiment of FIG. 5.

On the other hand, even where a vibration signal whose value is larger than the vibration threshold ST is entered, in some cases, the user may artificially generate a vibration signal to manipulate exercise data as shown in FIG. 7. Such scenario is additionally determined in step S511.

That is, where the vibration measurement is larger than the reference value in step S509, the regularity of the period when the vibration measurement becomes the peak is determined (S511).

FIG. 7 is a reference view illustrating another example in which manipulation of exercise data occurs in the embodiment of FIG. 5, wherein the waveform of a vibration signal is shown where the vibration signal is artificially generated using a machine, e.g., a motor.

As shown, where a vibration signal S(t) larger than the threshold ST is sensed but the vibration period T(n) of the vibration signal entered is generated constant for a predetermined time, i.e., regularity is observed, it can be considered that the vibration signal has artificially be created.

At this time, constant C for determining the deviation in vibration period when the peak of vibration signal occurs is set as a reference for determining the regularity of vibration signal. C may be varied per fitness machine depending on the properties of the fitness machine.

Thus, the reference value (i.e., constant C) for determining whether exercise data is manipulated as per the driving characteristics of the fitness machine may previously be set, and recorded or stored in the storage unit 80 of the exercise data manipulation preventing device. Here, reference value C is a reference for grasping the unique features of the fitness machine per type, manufacturer, or model, and this value is previously set per date of manufacture, manufacturer, or model name of the fitness machine and stored in the storage unit. Accordingly, the unique features of the fitness machine may be grasped through the fitness machine information, and reference value C corresponding to a unique feature grasped may be extracted.

Assuming that C has previously been set and determined, n is an integer, and the consecutive times when the peaks of vibration measurements occur are T(n), T(n+1), and T(n+2), period λ(n) when the peak of the vibration measurement occurs may be determined by Equation 1:

$$T(n+1) - T(n) = \lambda(n) \quad \text{[Equation 1]}$$
$$T(n+2) - T(n+1) = \lambda(n+1)$$
$$\ldots$$

Thereafter, as described above, it is determined whether the deviation between periods when the consecutive vibration peaks occur is shown substantially constant. That is, if the deviation between the vibration periods steadily occurs which is smaller than the minimum threshold C as shown in Equation 2 below, the vibration may be determined to have artificially been generated.

$$|\lambda(n)-\lambda(n+1)|<C \quad \text{[Equation 2]}$$

As a result of the determination in step S511, if the deviation in vibration period is smaller than C, the exercise data is determined to have been manipulated or be abnormal (S513), and if the deviation in vibration period is larger than C, the exercise data is determined to be normal, and the exercise data is stored (S517).

Figure 8:
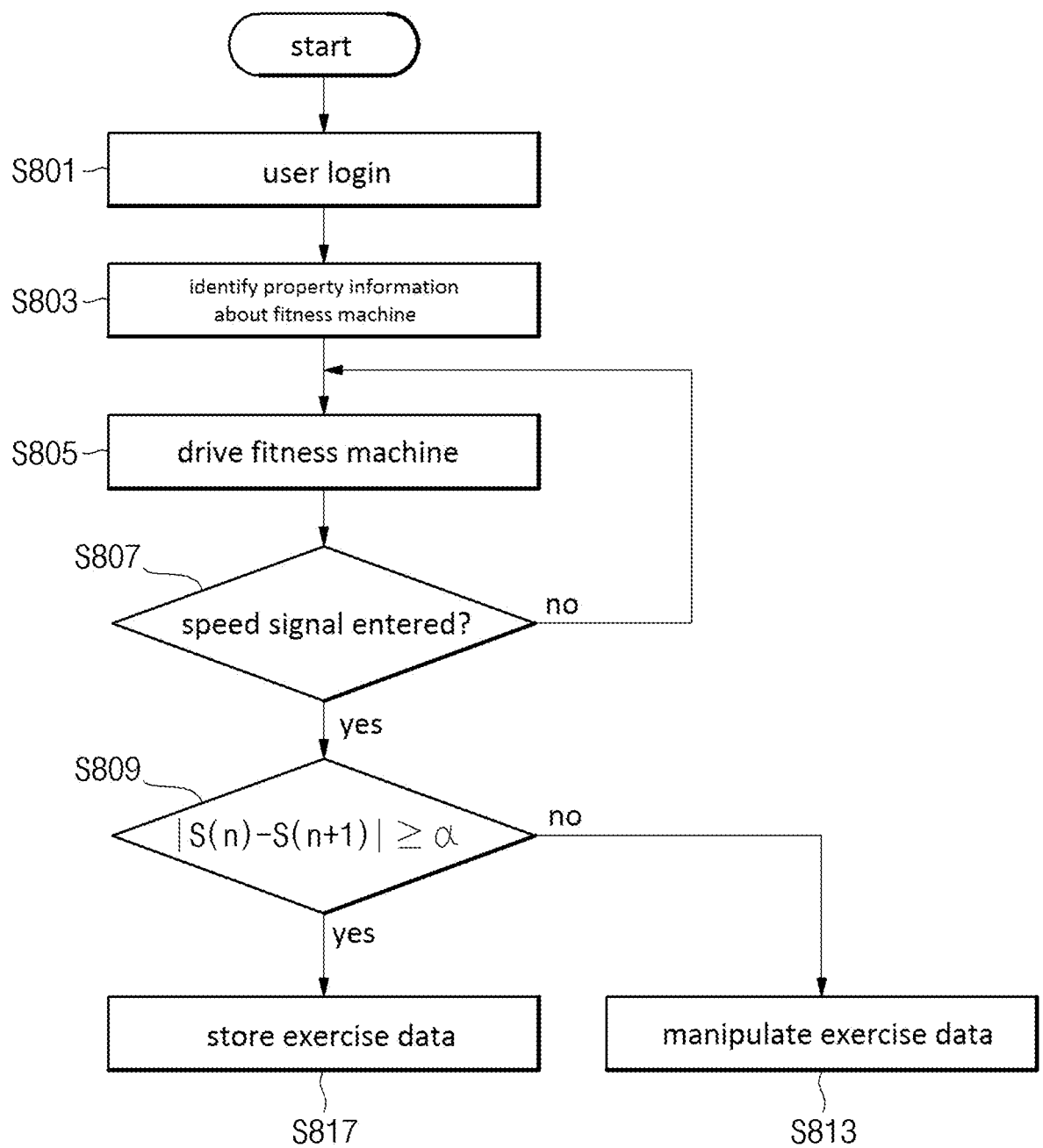
FIG. 8 is a flowchart illustrating sequentially a method for preventing manipulation of exercise data according to a second embodiment of the present disclosure.

FIG. 8 is a flowchart sequentially illustrating a method for preventing manipulation of exercise data according to a second embodiment of the present disclosure, wherein an example of applying the method to a human-powered fitness machine, such as a cycling machine or stepper is shown as an example.

First, the exercise data manipulation preventing device receives login information from the user (S801). The user may continuously enter his exercise data to the database and manage the exercise data by logging into his account and doing exercise. Or, if he uses an exer-gaming fitness machine, he may log in and enjoy game and exercise or hold a competition or event with other users.

The exercise data manipulation preventing device identifies fitness machine information for identifying unique features of the fitness machine for which the user logs in (S803). The fitness machine information may include the model number, ID, or serial number of the fitness machine or any other unique information from which the features of the fitness machine may be identified.

The storage unit 80 of the exercise data manipulation preventing device records or stores reference values for determining whether exercise data is manipulated as per the driving characteristics of the fitness machine. Here, the reference values may be a reference for grasping the unique features of the fitness machine per type, manufacturer, or model of the fitness machine, and the reference values may previously be stored per date of manufacture, manufacturer, or model and stored in the storage unit. Accordingly, the unique features of the fitness machine may be grasped through the fitness machine information, and reference values corresponding to the grasped unique features may be extracted.

In the instant embodiment, a reference value α for determining a deviation in exercise speed as per the driving of the fitness machine is previously set and stored in the storage unit, and the reference value α currently suitable for the fitness machine is extracted by identifying the feature information about the fitness machine.

Thereafter, if the fitness machine is driven, exercise data is entered (S805). The instant embodiment relates to preventing manipulation of exercise data in human-powered fitness machines. Indoor bikes, elliptical trainers, or other most fitness machines feature being human-powered rather than machine powered. Accordingly, the fitness machine should be driven by an external power machine, e.g., a motor, to manipulate exercise data in such fitness machine. If the fitness machine is driven by the external power machine to artificially generate exercise data, the speed of exercise measured from the fitness machine becomes very constant. In contrast, if one actually does exercise, the exercise speed entails more or less fluctuations. Thus, preventing manipulation of exercise data in the human-powered fitness machines requires a series of steps of obtaining speeds at predetermined cycles and determining that data has been manipulated when deviations in speed is too constant.

That is, if entry of a speed signal of the fitness machine is identified (S807), exercise speed data generated through the driving of the fitness machine is measured at each predetermined period. At this time, assuming the exercise speed data is S(t) and consecutive pieces of exercise speed data measured at each period T are S(n), S(n+1), S(n+2), and S(n+3), the regularity of the exercise speed deviation is determined by Equation 3 below (S809).

$$|S(n)-S(n+1)| \geq \alpha \quad \text{[Equation 3]}$$

Figure 9:
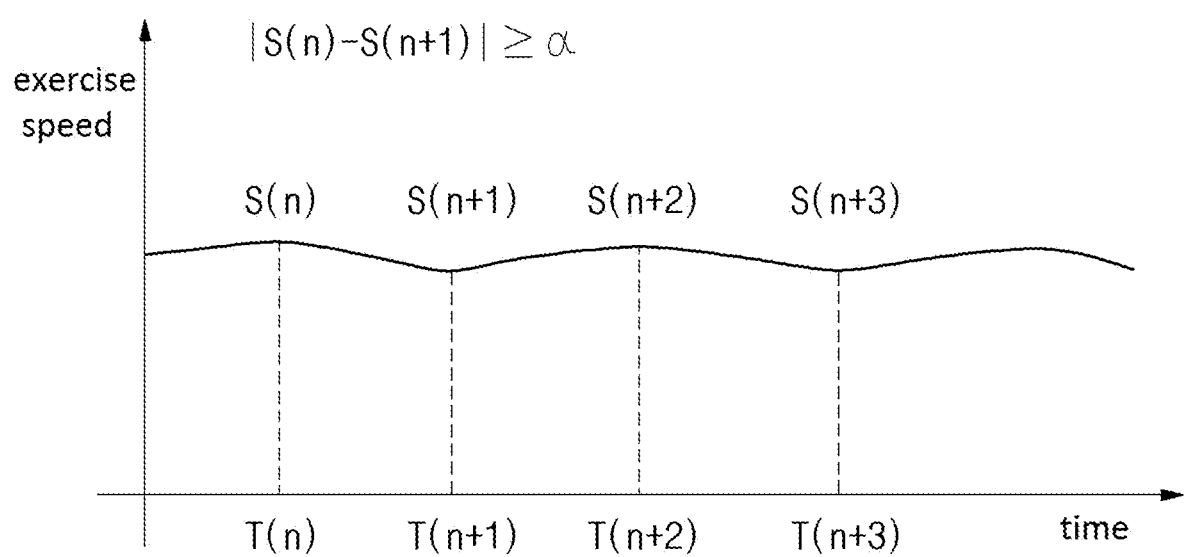
FIG. 9 is a reference view illustrating an example in which exercise data is normally generated in the embodiment of FIG. 8.

FIG. 9 is a reference view illustrating an example in which exercise data is normally generated in the embodiment of FIG. 8.

As shown, since the exercise speed data is natural data artificially generated, the exercise speeds are not constant, causing a deviation. Accordingly, it can be shown that the deviations between pieces of exercise speed data (S(n), S(n+1), S(n+2), and S(n+3)) obtained for a predetermined time and measured at each period T meet Equation 3 above.

Figure 10:
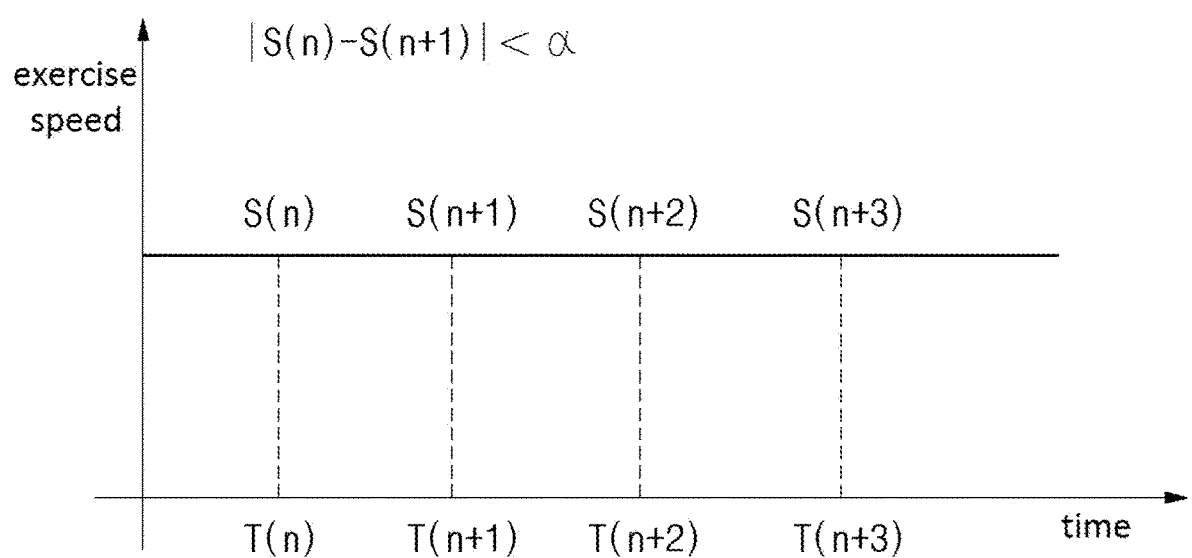
FIG. 10 is a reference view illustrating an example in which exercise data is abnormally generated in the embodiment of FIG. 8.

However, if the exercise speed data is entered substantially constant as shown in FIG. 10, it can be considered as exercise data generated by an artificial means, e.g., an electrical motor, and thus, it can be shown that it fails to meet Equation 3.

As set forth above, as a result of the determination in step S809, upon meeting Equation 3, the exercise data is determined to be normal exercise data and stored (S817). Upon failing to meet Equation 3, the exercise data is determined to be manipulated exercise data or abnormal exercise data (S813) and the data is not stored.

It will be understood that each or combinations of the blocks in the flowchart described herein may be performed by computer program instructions. The computer program instructions may be equipped in processors of general-purpose computers, special computers, or other programmable data processing equipment. Thus, the instructions performed through the processors of the computers or other programmable data processing equipment generate means to perform the functions described with reference to the flowchart blocks. The computer programmable instructions may also be stored in computer-available or computer-readable memories oriented to computers or other programmable data processing equipment to implement functions in a particular manner. Thus, the instructions stored in the computer-available or computer-readable memories may generate product items embedded with instruction means to perform the functions described in connection with the flowchart blocks. The computer program instructions may be equipped on computers or other programmable data processing equipment. Thus, instructions generating a process executed on a computer and having a series of operations or steps performed on a computer or other programmable data processing equipment and executing the computer or other programmable data processing equipment may provide steps for executing the functions described in connection with the flowchart blocks.

Each block may denote a module, segment, or part of code including one or more executable instructions for executing a specified logical function(s). In some alternatives, it should be noted that the functions mentioned in the blocks may be generated out of order. For example, two consecutive blocks may be performed substantially simultaneously or sometimes in reverse order depending on their corresponding functions.

As used herein, the term "unit" means a software or hardware component, such as FPGA or ASIC. The " . . . unit" performs some role. However, the term "unit" is not essentially limited to software or hardware. For example, " . . . unit" may be configured in an addressable storage medium or configured to reproduce one or more processors. Accordingly, " . . . unit" includes software components, object-oriented software components, class components, task components, processes, functions, properties, procedures, subroutines, program code segments, drivers, firmware, microcode, circuits, data, database, data architectures, tables, arrays, and variables. The function provided in the "units" may be combined into a smaller number of components and "units" or they, together with additional components, may be split into "units." Besides, the components and "units" may be implemented to reproduce one or more CPUs in the device or secure multimedia card.

It would be appreciated by one of ordinary skill in the art that various changes may be made to the embodiments disclosed herein without changing the technical spirit or essential features. Thus, it should be understood that the embodiments of the disclosure are exemplary in all aspects but not limiting. It should be understood that the scope of the present disclosure is defined not by the description but by the appended claims, and all changes, modifications, or equivalents thereto also belong to the scope of the present disclosure.

Meanwhile, while preferred embodiments of the present disclosure have been shown and described using particular terms in the specification and the drawings, this is simply for a better understanding of the present disclosure and should not be construed as limiting the present disclosure. It is apparent to one of ordinary skill in the art that other various changes may be made to the embodiments disclosed herein without departing from the scope of the present disclosure.

What is claimed is:

1. A method for analyzing a user's exercise data generated from a fitness machine, the method comprising the steps of:
    receiving the user's login information;
    identifying fitness machine information for identifying a unique feature of the fitness machine to which the user logs in;
    identifying a reference value for determining whether the exercise data is manipulated as per the feature of the fitness machine through the fitness machine information, the reference value set based on at least one or more of the type, manufacturer, and model name of the fitness machine;
    determining whether the fitness machine is driven;
    if the fitness machine is identified to be driven, identifying a vibration measurement obtained for the fitness machine through a vibration sensor for a predetermined time; and
    determining that the user's exercise data is manipulated and refraining from storing the exercise data when the vibration measurement is smaller than the reference value, or when a peak of the vibration measurement is determined to irregularly occur.

2. The method of claim 1, wherein whether the fitness machine is driven is identified based on whether a speed signal generated from the fitness machine is entered.

3. The method of claim 1, wherein if the vibration measurement is larger than the reference value in the step of determining whether the exercise data is manipulated, the user is determined to normally do exercise, and the method further comprises the step of storing the exercise data generated from the fitness machine.

4. The method of claim 1, wherein the reference value includes a minimum vibration ST of the fitness machine generated as the user drives the fitness machine based on the fitness machine feature and a constant C for determining a deviation in the vibration period when a fitness machine vibration peak occurs.

5. The method of claim 4, wherein when n is an integer, T(n) is the time when the peak of the vibration measurement occurs, and a period $\lambda(n)$ when the peak of the vibration measurement occurs meets an equation: $T(n+1)-T(n)=\lambda(n)$, if the vibration measurement is larger than the reference value in the step of determining whether the exercise data is manipulated, the period $\lambda(n)$ meets the following equation, $|\lambda(n)-\lambda(n+1)|<C$, and is generated for a predetermined time, the exercise data is determined to be manipulated.

6. The method of claim 1, wherein the fitness machine is a treadmill.

7. A method for analyzing a user's exercise data generated from a human-powered fitness machine, the method comprising the steps of:
    receiving the user's login information;
    identifying fitness machine information for identifying a unique feature of the fitness machine to which the user logs in;
    identifying a reference value for determining whether the exercise data is manipulated as per the feature of the fitness machine through the fitness machine information, the reference value set based on at least one or more of the type, manufacturer, and model name of the fitness machine;
    measuring exercise speed data generated through driving of the fitness machine at each predetermined period;
    comparing a deviation between pieces of the measured exercise speed data with the reference value to determine whether the user's exercise data is manipulated; and
    determining that the user's exercise data is manipulated and refraining from storing the exercise data when the deviation is smaller than the reference value, or when a peak of the deviation is determined to irregularly occur.

8. The method of claim 7, wherein if the deviation between the pieces of the exercise speed data is larger than the reference value in the step of determining whether the exercise data is manipulated, the user is determined to normally do exercise, and the method further comprises the step of storing the exercise data generated from the fitness machine.

9. The method of claim 7, wherein the reference value includes a constant a for determining the deviation in the exercise speed generated as the user drives the fitness machine based on the fitness machine feature.

10. The method of claim 9, wherein when n is an integer, and S(n) is a value obtained by measuring the exercise speed data at each predetermined period, if the measured exercise speed data S(n) meets the following equation, $|S(n)-S(n+1)|<\alpha$, and occurs for a predetermined time or more in the step of determining whether the exercise data is manipulated, the exercise data is determined to be manipulated.

11. The method of claim 7, wherein the fitness machine is a stepper, a cycling machine, an indoor cycling bike, or an air walk trainer.

12. A device for analyzing a user's exercise data generated from a fitness machine, comprising:
    a sensor mounted in or near a driver of the fitness machine to detect a vibration as per the user's exercise;
    a storage unit storing a reference value for determining whether the exercise data is manipulated as per a driving feature of the fitness machine, the reference value set based on at least one or more of the type, manufacturer, and model name of the fitness machine;
    an exercise data determiner comparing a vibration measurement obtained for the fitness machine through the sensor with the reference value to determine whether the user's exercise data is manipulated if the fitness machine is identified to be driven; and
    a controller receiving fitness machine information for identifying a unique feature of the fitness machine, extracting the reference value corresponding to the fitness machine from the storage unit, receiving a result of determining whether the user's exercise data is normal from the exercise data determiner, and performing control to store the received exercise data if the exercise data is determined to be normal and not to store the received exercise data if the exercise data is determined to be abnormal, the controller determining that the user's exercise data is manipulated and refraining from storing the exercise data when the vibration measurement is smaller than the reference value, or when a peak of the vibration measurement is determined to irregularly occur.

* * * * *